US012427266B1

United States Patent
Hee-Hanson et al.

(10) Patent No.: US 12,427,266 B1
(45) Date of Patent: Sep. 30, 2025

(54) NEEDLE SHROUD LATCH FOR INJECTION DEVICES

(71) Applicant: Genzyme Corporation, Cambridge, MA (US)

(72) Inventors: Alexander Hee-Hanson, Melbourn (GB); Thomas Lever, Melbourn (GB); Michael Parrott, Melbourn (GB); Robert Wilson, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/619,991

(22) Filed: Mar. 28, 2024

(51) Int. Cl.
*A61M 5/32* (2006.01)
*A61M 5/20* (2006.01)

(52) U.S. Cl.
CPC ............ *A61M 5/3232* (2013.01); *A61M 5/20* (2013.01); *A61M 5/3272* (2013.01)

(58) Field of Classification Search
CPC ........ A61M 2005/3267; A61M 5/3271; A61M 5/3272
See application file for complete search history.

(56) References Cited

U.S. PATENT DOCUMENTS

| | | | |
|---|---|---|---|
| 4,900,311 A | 2/1990 | Stern et al. | |
| 5,088,986 A | 2/1992 | Nusbaum | |
| 5,290,256 A | 3/1994 | Weatherford et al. | |
| 5,688,241 A | 11/1997 | Asbaghi | |
| 7,597,685 B2 | 10/2009 | Olson | |
| 8,016,797 B2 | 9/2011 | Gratwohl et al. | |
| 8,821,451 B2 | 9/2014 | Daniel | |
| 9,199,038 B2 | 12/2015 | Daniel | |
| 9,408,976 B2 | 8/2016 | Olson et al. | |

(Continued)

FOREIGN PATENT DOCUMENTS

| | | |
|---|---|---|
| WO | WO 2011/123024 A1 | 10/2011 |
| WO | WO 2014/115241 A1 | 7/2014 |

(Continued)

OTHER PUBLICATIONS

Needle-based injection systems for medical use requirements and test methods, Part 1: Needle injection systems, ISO 11608-1:2014(E), Third Edition, Switzerland, ISO, Dec. 15, 2014, pp. 1-13.

(Continued)

*Primary Examiner* — Emily L Schmidt
(74) *Attorney, Agent, or Firm* — Fish & Richardson P.C.

(57) ABSTRACT

An injection device comprises: an injection device body; a needle shroud comprising a shroud pin; and a collar rotatable with respect to the injection device body and comprising a cam track. During retraction of the needle shroud, a first portion of the cam track guides the shroud pin to a hold position and cause the collar to rotate relative to the injection device body from a first position to a second position. During a subsequent extension of the needle shroud, a second portion of the cam track guides the shroud pin from the hold position to a final position and causes the collar to further rotate relative to the injection device body from the second position to a third position, the second portion comprising a blocking portion configured to prevent extension of the needle shroud from the injection device body when the collar is held in the second position.

19 Claims, 10 Drawing Sheets

(56) References Cited

U.S. PATENT DOCUMENTS

| | | |
|---|---|---|
| 9,498,579 B2 | 11/2016 | Ruan |
| 9,662,452 B2 | 5/2017 | Daniel |
| 9,867,940 B2 | 1/2018 | Holmqvist et al. |
| 9,919,107 B2 | 3/2018 | Imai et al. |
| 10,420,898 B2 | 9/2019 | Daniel |
| 11,369,751 B2 | 6/2022 | Ruan et al. |
| 11,944,787 B2 | 4/2024 | Franke |
| 12,274,866 B1 | 4/2025 | Hee-Hanson et al. |
| 12,274,871 B1 | 4/2025 | Hee-Hanson et al. |
| 12,274,872 B1 | 4/2025 | Hee-Hanson et al. |
| 12,274,875 B1 | 4/2025 | Hee-Hanson et al. |
| 2006/0276756 A1 | 12/2006 | Francavilla |
| 2010/0268170 A1 | 10/2010 | Carrel et al. |
| 2012/0203186 A1 | 8/2012 | Vogt et al. |
| 2013/0041328 A1* | 2/2013 | Daniel ............... A61M 5/31511 604/228 |
| 2013/0096512 A1 | 4/2013 | Ekan et al. |
| 2013/0123710 A1 | 5/2013 | Ekman et al. |
| 2013/0261559 A1 | 10/2013 | Werbickas |
| 2013/0289525 A1 | 10/2013 | Kemp et al. |
| 2014/0025013 A1 | 1/2014 | Dowds et al. |
| 2015/0190580 A1* | 7/2015 | Imai .................. A61M 5/31505 604/220 |
| 2015/0258283 A1 | 9/2015 | Imai et al. |
| 2016/0089498 A1 | 3/2016 | Daniel |
| 2017/0239427 A1 | 8/2017 | Mehawej et al. |
| 2018/0064875 A1 | 3/2018 | Holmqvist |
| 2018/0104414 A1 | 4/2018 | Karlsson et al. |
| 2018/0361082 A1 | 12/2018 | Sall et al. |
| 2020/0179614 A1 | 6/2020 | McElroy et al. |
| 2020/0289755 A1 | 9/2020 | Franke |
| 2021/0093796 A1 | 4/2021 | Finkelstein et al. |
| 2021/0236732 A1 | 8/2021 | Chu et al. |
| 2021/0244887 A1 | 8/2021 | Halseth |
| 2021/0393886 A1 | 12/2021 | Nicolas et al. |
| 2022/0176042 A1 | 6/2022 | Belisle |
| 2022/0387719 A1 | 12/2022 | Wang et al. |
| 2022/0395642 A1* | 12/2022 | Karlsson ............. A61M 5/2033 |
| 2023/0338662 A1 | 10/2023 | Böstrom |
| 2024/0139430 A1* | 5/2024 | Chansavang ....... A61M 5/3271 |
| 2024/0165346 A1 | 5/2024 | Chansavang et al. |

FOREIGN PATENT DOCUMENTS

| | | |
|---|---|---|
| WO | WO 2021/008839 A1 | 1/2021 |
| WO | WO 2023/104512 A1 | 6/2023 |
| WO | WO 2023/151957 A1 | 8/2023 |

OTHER PUBLICATIONS

U.S. Appl. No. 18/619,754, filed Mar. 28, 2024, Alexander Hee-Hanson.

U.S. Appl. No. 18/620,210, filed Mar. 28, 2024, Alexander Hee-Hanson.

U.S. Appl. No. 18/620,586, filed Mar. 28, 2024, Alexander Hee-Hanson.

U.S. Appl. No. 18/619,996, filed Mar. 28, 2024, Alexander Hee-Hanson.

U.S. Appl. No. 18/620,097, filed Mar. 28, 2024, Alexander Hee-Hanson.

International Search Report and Written Opinion in International Appln. No. PCT/US2025/021782, mailed on May 30, 2025, 17 pages.

International Search Report and Written Opinion in International Appln. No. PCT/US2025/021785, mailed on Jun. 13, 2025, 18 pages.

International Search Report and Written Opinion in International Appln. No. PCT/US2025/021718, mailed on May 8, 2025, 16 pages.

International Search Report and Written Opinion in International Appln. No. PCT/US2025/021774, mailed on May 8, 2025, 17 pages.

International Search Report and Written Opinion in International Appln. No. PCT/US2025/021787, mailed on May 15, 2025, 18 pages.

International Search Report and Written Opinion in International Appln. No. PCT/US2025/021778, mailed on Jun. 27, 2025, 19 pages.

* cited by examiner

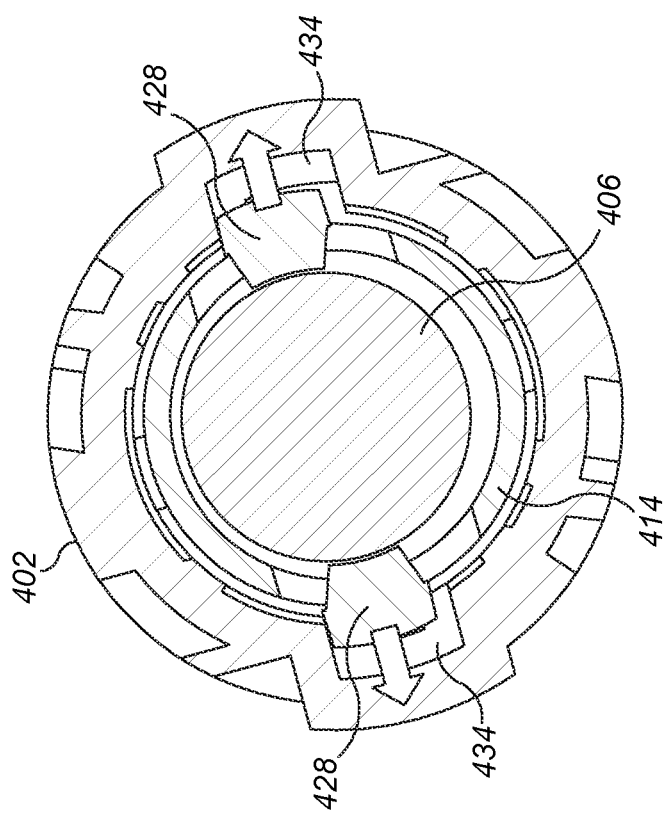
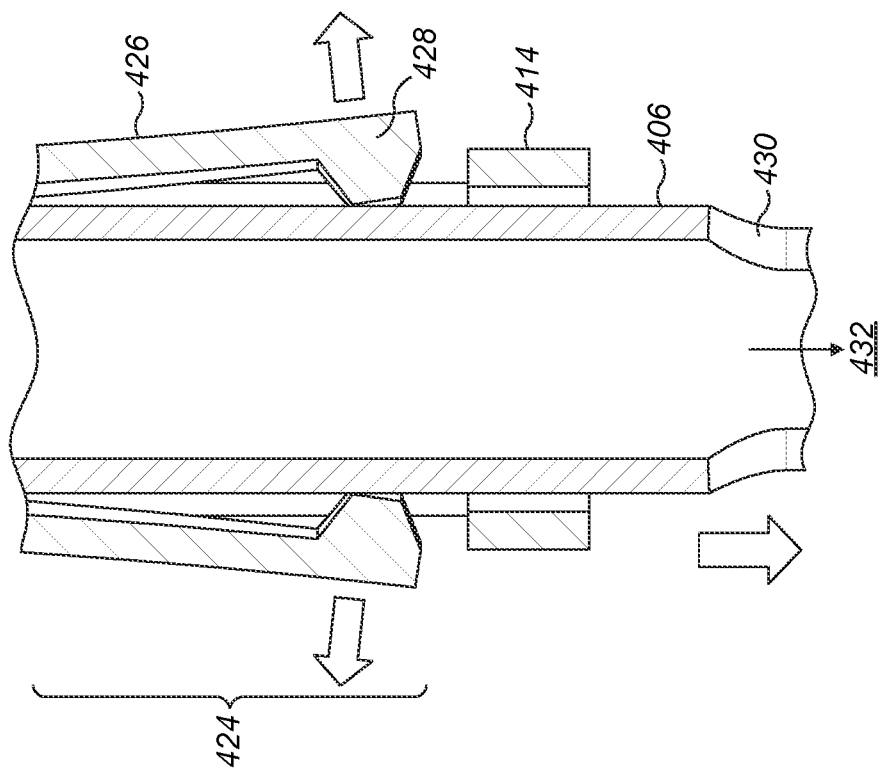
FIG. 4D
FIG. 4C

NEEDLE SHROUD LATCH FOR INJECTION DEVICES

TECHNICAL FIELD

This application relates to an injection device for delivery of a medicament, e.g., to an auto-injector device.

BACKGROUND

An auto-injector may be described as a device which completely or partially replaces the activities involved in drug delivery from a standard syringe. Typically, these include removal of the protective syringe cap, insertion of the needle, injection of drug and possibly removal and shielding of the used needle. Administering an injection is a process which presents several risks and challenges, both mental and physical. The use of an auto-injector can bring many benefits for the user and healthcare professional.

Many auto-injectors have a needle cover which is biased by a spring (the needle cover spring) to extend out of the device. On removal of the device from the injection site, this spring automatically extends the needle cover past the needle to provide needle shielding. On activation of the device, the needle cover is pushed into the device. A user has to provide the force to actuate the needle cover, overcome the activation mechanism forces and compress the needle cover spring (activation force). During drug delivery the user must hold the device at the injection site and apply a force (hold force) parallel to the needle cover direction of extension to react the needle cover biasing member.

If the activation or hold force is too high or has a certain profile, it can lead to use issues such as incorrectly thinking the device is not working, inadvertent early removal or a wet injection site. Some users have difficulty applying this hold force during the full drug delivery time. This results in pain, discomfort, a wet injection site, early device removal and partial drug delivery.

SUMMARY

According to a first aspect of the present disclosure, there is provided an injection device comprising:
an injection device body;
a needle shroud retractable into the injection device body comprising a shroud pin; and
a collar rotatable with respect to the injection device body and comprising a cam track engageable with the shroud pin,
wherein the cam track comprises:
a first portion configured to, during retraction of the needle shroud into the injection device body, guide the shroud pin from an initial position to a hold position and cause the collar to rotate relative to the injection device body from a first position to a second position; and
a second portion configured to, during extension of the needle shroud from the injection device body subsequent to the retraction, guide the shroud pin from the hold position to a final position and cause the collar to further rotate relative to the injection device body from the second position to a third position, and
wherein the second portion comprises a blocking portion configured to prevent extension of the needle shroud from the injection device body when the collar is held in the second position.

The first portion of the cam track may comprise a first angled cam track edge arranged to convert at least a portion of proximal axial motion of the needle shroud into rotational motion of the collar.

The blocking portion may comprise a second angled cam track edge arranged to convert at least a portion of distal axial motion of the needle shroud into rotational motion of the collar.

The injection device may further comprise a plunger release mechanism, wherein the collar may be configured to be held in the second position temporarily by the plunger release mechanism.

The plunger release mechanism may comprise one or more toothed beams; the injection device may further comprise a plunger comprising one or more recesses, and a biasing means for biasing the plunger in a distal direction of the injection device; the one or more toothed beams may each comprise a tooth engageable with a respective recess of the one or more recesses of the plunger; and the one or more recesses and/or the one or more teeth may be shaped to urge the one or more toothed beams out of the one or more recesses when the plunger is moved in the distal direction of the injection device.

The collar may surround the one or more toothed beams to prevent the toothed beams from flexing outwardly when the collar is in the first position, thereby holding the plunger.

An internal surface of the collar may comprise one or more recesses arranged to allow the one or more toothed beams to flex outwardly when the collar is rotated to the second position, thereby to release the plunger.

The one or more toothed beams may be configured to engage the one or more recesses in the internal surface of the collar when the collar is in the second position, to hold the collar in the second position and prevent rotation of the collar.

The one or more toothed beams may be configured to be held in engagement with the one or more recesses in the internal surface of the collar by an outer surface of the plunger during distal movement of the plunger.

The injection device may further comprise a control spring to bias the needle shroud towards an extended position.

The shroud pin may extend inwardly from the needle shroud in a radial direction.

The injection device may further comprise a needle, wherein the needle shroud may be arranged to shroud the needle when in an extended position.

The injection device may further comprise a syringe containing a medicament.

According to a second aspect of the present disclosure, there is provided a collar for an injection device comprising a cam track engageable with a shroud pin of a needle shroud, wherein the cam track comprises:
a first portion configured to, during retraction of the needle shroud into an injection device body of the injection device, guide the shroud pin from an initial position to a hold position and cause the collar to rotate relative to the injection device body from a first position to a second position; and
a second portion configured to, during extension of the needle shroud from the injection device body subsequent to the retraction, guide the shroud pin from the hold position to a final position and cause the collar to further rotate relative to the injection device body from the second position to a third position, and wherein the second portion comprises a blocking portion configured to prevent extension of the needle shroud from the injection device body when the collar is held in the second position.

The first portion of the cam track may comprise a first angled cam track edge arranged to convert at least a portion of proximal axial motion of the needle shroud into rotational motion of the collar.

The blocking portion comprises a second angled cam track edge may be arranged to convert at least a portion of distal axial motion of the needle shroud into rotational motion of the collar.

The collar may be configured to be held in the second position temporarily by a plunger release mechanism.

The collar may be arranged to surround one or more toothed beams of the plunger release mechanism to prevent the toothed beams from flexing outwardly when the collar is in the first position, thereby holding the plunger.

An internal surface of the collar may comprise one or more recesses arranged to allow one or more toothed beams of the plunger release mechanism to flex outwardly when the collar is rotated to the second position, thereby to release the plunger.

The one or more recesses in the internal surface of the collar may be configured to be engaged by the one or more toothed beams when the collar is in the second position, to hold the collar in the second position and prevent rotation of the collar.

The shroud pin may extend inwardly from the needle shroud in a radial direction.

According to a third aspect of the present disclosure, there is provided a method for holding a needle shroud of an injection device during medicament delivery, the method comprising:

during retraction of the needle shroud into an injection device body of the injection device, guiding a shroud pin of the needle shroud from an initial position to a hold position using a first portion of a cam track of an injection device collar, the guiding causing the injection device collar to rotate relative to the injection device body from a first position to a second position;

holding the collar in the second position; and while the collar is held in the second position, preventing extension of the needle shroud from the injection device body using a blocking portion of the cam track.

The method may further comprise releasing the collar such that it is free to rotate from its second position, responsive to completion of a movement of a plunger of the injection device to dispense a medicament.

The method may further comprise, after the collar is released such that it is free to rotate, and during extension of the needle shroud from the injection device body subsequent to the retraction, guiding the shroud pin from the hold position to a final position using a second portion of the cam track of the injection device collar, the guiding causing the injection device collar to rotate relative to the injection device body from its second position to a third position.

The rotation of the collar from the first position to the second position may be in the same direction as the rotation of the collar from the second position to the third position.

The first portion of the cam track may comprise a first angled cam track edge arranged to convert at least a portion of proximal axial motion of the needle shroud into rotational motion of the collar.

The blocking portion may comprise a second angled cam track edge arranged to convert at least a portion of distal axial motion of the needle shroud into rotational motion of the collar.

The collar may be held in the second position by a plunger release mechanism of the injection device.

The plunger release mechanism may comprise one or more toothed beams; the injection device further may comprise a plunger comprising one or more recesses, and a biasing means for biasing the plunger in a distal direction of the injection device; the one or more toothed beams may each comprise a tooth engageable with a respective recess of the one or more recesses of the plunger; and the one or more recesses and/or the one or more teeth may be shaped to urge the one or more toothed beams out of the one or more recesses when the plunger is moved in the distal direction of the injection device.

The method may further comprise dispensing a medicament from a syringe of the injection device.

BRIEF DESCRIPTION OF THE FIGURES

Exemplary embodiments of the present disclosure are described with reference to the accompanying drawings, in which:

FIG. 4C shows a cut-away view of the plunger and rear casing of FIG. 4A during release of the plunger;

FIG. 4D shows an example of a cross section of the injection device of FIG. 4B in a plane through the teeth of the toothed beams during release of the plunger;

DETAILED DESCRIPTION

Figure 1:
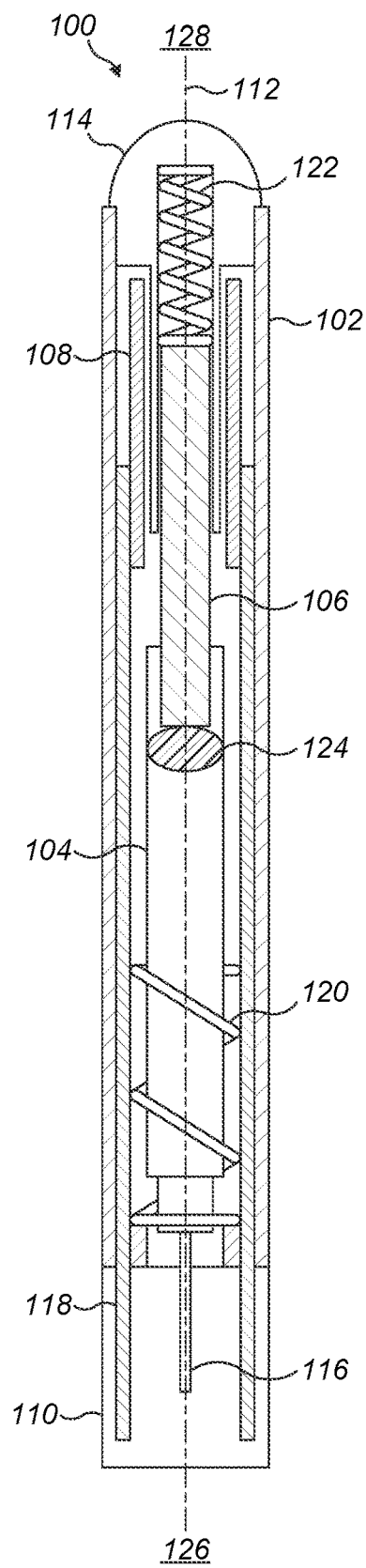
FIG. 1 shows a schematic example of a cross section of an injection device.

A drug delivery device (also referred to as an injection device), as described herein, may be configured to inject a medicament into a subject such as a human or animal. For example, delivery could be sub-cutaneous, intra-muscular, or intravenous. Such a device could be operated by a user, who may or may not be the subject. In examples where the user is not the subject, the user may be a care-giver such as a nurse or physician. The device can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a subject's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Auto-injectors require user actions to commence medicament delivery. One of these actions may involve a user placing a needle shroud (also referred to as a needle cover or needle sleeve) against an injection site of a subject and applying an axial force to the device to cause the needle shroud to retract into the housing of the device. As the needle shroud retracts into the housing, the needle of the device extends beyond the needle shroud and penetrates the injection site of the subject (e.g. the subject's skin). Medicament delivery may be automatically initiated in response to the retraction of the needle shroud or in response to some other action by the user, for example the user pressing a button on the device. Once medicament delivery has been initiated, a medicament delivery mechanism will cause medicament contained within the device to be injected into the subject via the needle. The user should hold the device steady with respect to the injection site during the course of medicament delivery to ensure the needle remains steady within the subject. This is to minimise pain and/or discomfort for the subject, and to prevent a wet injection site, early device removal and/or partial medicament delivery.

After the device is removed from injection site, many autoinjectors cover the needle with the needle shroud/needle cover, which is extended out of the device by a control spring. During activation of the device and while holding the device steady during medicament delivery, the user must counteract the biasing force applied by the control spring to the needle shroud. However, some users such as those with impaired dexterity may find it difficult to counteract the biasing force of the control spring, e.g., if they are required to hold the device steady for a relatively long period of time during medicament delivery. It may be beneficial to provide a device which is easier to handle during medicament delivery.

Injection devices described herein use a latch for holding a needle shroud in a retracted position during medicament delivery. The latch comprises a collar having a cam track comprising a blocking portion, and a shroud pin of the needle shroud. The cam track is configured to be engaged by the shroud pin. The collar is rotatable within an injection device body of the injection device such that retraction of the needle shroud into the injection device body (e.g., as the device is pressed against an injection site) causes the collar to rotate, due to engagement between the shroud pin and the cam track. Once the collar has been rotated, engagement between the shroud pin and the blocking portion prevents extension of the needle shroud from the injection device body. The collar may be temporarily held by a plunger release mechanism, which prevents rotation of the collar until medicament delivery is complete. In instances where the injection device comprises a control spring for biasing the needle shroud to extend out of the injection device body, engagement between the shroud pin and the blocking portion prevents a biasing force provided by the control spring to the needle shroud from being transferred to the injection site of the subject. As such, the user of the device may no longer need to counteract the biasing force of the control spring to hold the device steady against the injection site. The device may therefore be easier to handle during medicament delivery, for example by users with impaired dexterity.

FIG. 1 shows a schematic example of a cross section of an injection device 100 according to one or more aspects of the present disclosure. The injection device 100 is configured to inject a medicament into a subject. The injection device 100 comprises an outer casing 102 (also referred to as a housing or injection device body) that encloses a reservoir 104, a plunger 106 and a rotatable collar 108. The reservoir 104 typically contains the medicament to be injected, and may, for example, be in the form of a syringe. The injection device 100 can also include a cap assembly 110 that can be detachably mounted to the outer casing 102. Typically a user must remove cap 110 from the outer casing 102 before device 100 can be operated.

As shown, casing 102 is substantially cylindrical and has a substantially constant diameter along the longitudinal axis of the device 100. The injection device 100 has a distal region 126 and a proximal region 128. The term "distal" refers to a location that is relatively closer to a site of injection, and the term "proximal" refers to a location that is relatively further away from the injection site.

The outer casing 102 is closed at a proximal end by a rear casing 114. A needle 116 and a retractable needle shroud 118 (also referred to as a "needle sleeve" or "needle cover") extend from a distal end of the outer casing 102. The retractable needle shroud 118 is biased axially in the distal direction of the injection device 100, for example using a control spring 120. The needle shroud 118 is coupled to the outer casing 102 to permit axial movement of needle shroud 118 relative to the outer casing 102. For example, the shroud 118 can move in a longitudinal direction parallel to longitudinal axis 112. Specifically, movement of shroud 118 in a proximal direction relative to the casing 102 can cause a needle 116 to extend from distal region of the casing 102, and outside a distal end of the shroud 118.

The plunger 106 is biased towards the distal end of the injection device 100 by a biasing means, for example comprising a drive spring 122. The plunger 106 is retained in an initial position by a combination of the rear casing 114 and the collar 108, preventing the biasing means from displacing the plunger 106 in the distal direction. An example of such a retention mechanism is described in relation to FIGS. 4A to 4F. Activation of the injection device 100 causes the collar 108 to rotate, which releases the plunger 106. Once released, the biasing means causes the plunger 106 to move in the distal direction (i.e., towards the needle 116 end of the injection device 100). The plunger 106 contacts a stopper 124 in the reservoir 104, displacing the stopper 124 in the distal direction and causing medicament stored in the reservoir 104 to be expelled from the injection device 100 via the needle 116.

Activation of the injection device 100 can occur via several mechanisms. For example, the needle 116 may be fixedly located relative to the casing 102 and initially be located within an extended needle shroud 118. Proximal movement of the needle shroud 118 by placing a distal end of the shroud 118 against an injection site of the subject and moving the casing 102 in a distal direction will uncover the distal end of the needle 116. Such relative movement allows the distal end of the needle 116 to extend into the injection site. Such insertion is termed "manual" insertion as the needle 116 is manually inserted via the user's manual movement of the casing 102 relative to shroud 118. Retraction of the shroud 118 into the casing 102 causes the collar 108 to rotate, releasing the plunger 106.

Another form of activation is "automated", whereby the needle 116 moves relative to casing 102. Such insertion can be triggered by movement of the shroud 118 and/or by another form of activation, such as, for example, user actuation of a button (not shown) of the injection device 100.

Typically, the user presses the needle shroud 118 against an injection site to push the needle shroud 118 at least partially into the device casing 102. The exposed needle 116 is pushed into the injection site of the subject. In a holding position, medicament is automatically dispensed from the needle 116 via an automated mechanism. A user must typically hold the needle shroud 118 in the holding position for a predetermined period of time, to ensure that the correct dose of medicament is dispensed from the device 100, before removing the device 100 from the injection site.

The spring biasing force from the control spring 120 against which the user must apply a force to move the needle shroud 118 is one component of an "activation force" of the device 100. The activation force refers to the force or force profile that the user must exert on the device 100 to move the needle shroud 118 from the extended position shown in FIG. 1 to a retracted position within the casing 102 for medicament delivery. If this force or force profile is not well balanced, it can lead to difficulty in activating the device 100 for some users, or increase the pain or anxiety associated with using the device 100.

Following injection, the needle 116 can be retracted within the shroud 118. Retraction can occur when the shroud 118 moves distally under the biasing of the control spring 120 as a user removes the device 100 from the injection site of the subject. Once a distal end of the shroud 118 has moved past a distal end of the needle 116 such that the needle 116 is covered, the shroud 118 may be locked in its extended position to prevent any (substantial) proximal movement of the shroud 118 relative to the casing 102 (i.e., preventing any movement of the shroud 118 that would uncover the needle 116). The shroud 118 may be locked by a needle shroud non-return element (not shown), such as a catch.

Figure 2:
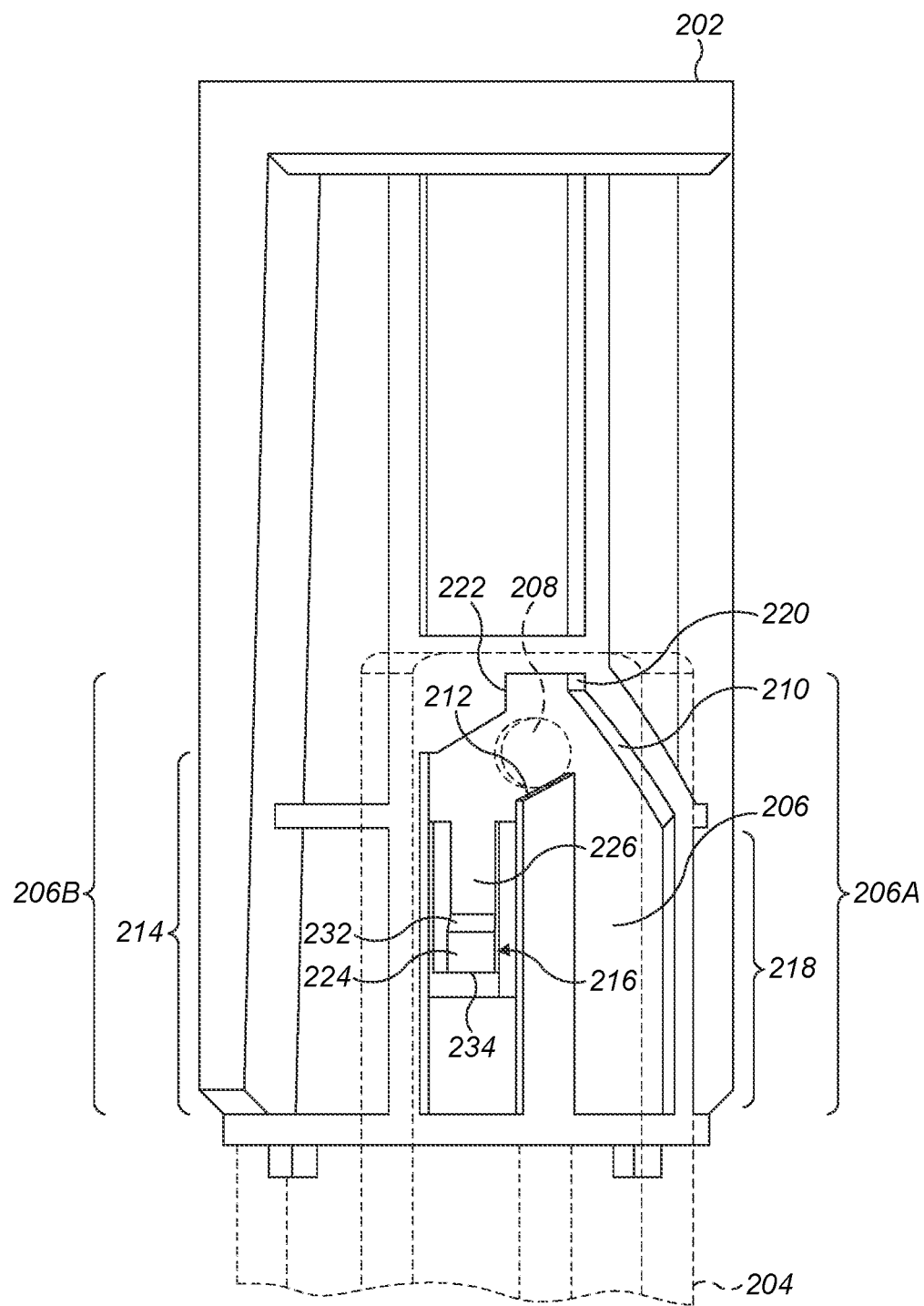
FIG. 2 shows an example of collar and needle shroud for an injection device.

FIG. 2 shows an example of collar 202 and needle shroud 204 for an injection device, e.g., the injection device 100 of FIG. 1, wherein the collar 202 and needle shroud may correspond to the collar 108 and needle shroud 118 of FIG. 1. The collar 202 may be a cylindrical collar that surrounds at least a part of the injection device, e.g., a portion of a casing (such as a portion of rear casing 114 shown in FIG. 1), of the injection device. The collar 202 comprises a cam track 206 on its outer surface that engages with a shroud pin 208 of the needle shroud 204. The shroud pin 208 may extend inwards from the needle shroud 204 in a radial direction, perpendicular to the longitudinal axis of the injection device and towards the collar 202, from a portion of the needle shroud 204 surrounding the collar 202.

The cam track 206 is configured to cooperate with the shroud pin 208 to guide the shroud pin 208 from an initial position to a hold position during retraction of the needle shroud 204 into the injection device, i.e., when the user is pressing the device against the injection site of a subject. During this retraction, the cam track 206 causes the collar 202 to rotate relative to the injection device body (i.e., relative to the casing 102). In the example shown, the collar 202 is configured to rotate from left to right, e.g., anticlockwise when viewed from above. The cam track 206 is further configured to cooperate with the shroud pin 208 to guide the shroud pin 208 from the hold position to a final (locked) position during extension of the needle shroud 204 out of the injection device after use, i.e., when the user is removing the device from the injection site after the completion of medicament delivery. The cam track 206 may be further configured to prevent retraction of the shroud 204 after the shroud pin 208 has reached the final position, i.e., after the device is removed from the injection site, using a non-return element 216 such as a catch.

In the example shown, the cam track 206 comprises a first portion 206A that causes the collar 202 to rotate by a first angle during retraction of the needle shroud 204 into the casing, from a first (rotational) position of the collar 202 (with respect to the needle shroud 204 and injection device body) to a second (rotational) position of the collar 202 (with respect to the needle shroud 204 and injection device body). The first portion 206A may comprise an initial cam track portion 218 that is aligned with the longitudinal axis of the injection device, i.e., parallel with the longitudinal axis of the injection device. The first portion 206A further comprises a first angled portion 210 of the cam track 206 comprising a first angled cam track edge (also referred to herein as a "ramp"). The first angled portion 210 is angled with respect to the longitudinal axis of the injection device such that the shroud pin 208 applies a force to the collar 202 during at least a portion of the retraction of the needle shroud 204 into the injection device body, causing the collar 202 to rotate from its first position to its second position. The first portion 206A may further comprise a final portion 220 that is aligned with the longitudinal axis of the injection device, i.e., parallel with longitudinal axis of the injection device.

Once the collar 202 has rotated to its second position shown in FIG. 2, it may be held in the second position by a plunger release mechanism, as described later in relation to FIGS. 4A-F. In response to the collar 202 having been rotated to its second position, the plunger release mechanism may be configured to engage the collar 202 to prevent the collar 202 from rotating further. The plunger release mechanism may hold the collar 202 in its second position temporarily, for example during a movement of a plunger (e.g., plunger 106) of the device during medicament delivery. Once the movement of the plunger is complete (e.g., corresponding to the completion of medicament delivery), the plunger release mechanism may release the collar 202 so that it is no longer held in the second position and is free to rotate again.

In the example shown, the cam track 206 comprises a second portion 206B that causes the collar to rotate (when the collar 202 is not held from rotation by the plunger release mechanism) by a second angle during extension of the needle shroud 204 from the casing, from the second position shown in FIG. 2 to a third (rotational) position (with respect to the needle shroud 204 and injection device body). The second portion 206B may comprise an initial portion 222 of the cam track 206 that is aligned with the longitudinal axis of the injection device, and which at least partially overlaps with the final portion 220 of the first portion 206A of the cam track 206.

The second portion 206B comprises a blocking portion 212 of the cam track 206. The blocking portion 212 is configured to prevent extension of the needle shroud 204 from the injection device body (i.e. distal movement of the needle shroud 204 from its retracted position) when the collar 202 is held in its second position by the plunger release mechanism.

The blocking portion 212 is arranged to be distal to the shroud pin 208 along an axis parallel to the longitudinal axis of the injection device, when the collar 202 is in its second position and the shroud pin 208 is in its hold position. Furthermore, the blocking portion 212 is arranged to abut the shroud pin 208 or be separated by only a small axial distance from the shroud pin 208 (for example 5 mm or less, 4 mm or less, 3 mm or less, 2 mm or less, or 1 mm or less) from the shroud pin 208 along an axis parallel to the longitudinal axis of the injection device, when the collar 202 is in its second position and the shroud pin 208 is in its hold position. As such, a distal movement of the needle shroud 204 and shroud pin 208 soon brings the shroud pin 208 into abutment with the blocking portion 212 (if not already abutting), to prevent (inhibit) further distal movement of the needle shroud 204. Since the collar 202 is prevented from rotating by the plunger release mechanism, a distal force applied by the shroud pin 208 against the blocking portion 212 is not transferred into rotation of the collar 202. The shroud pin 208 is prevented from moving distally by engagement with the blocking portion 212 and is prevented from rotating the collar 202 to move the blocking portion 212 out of engagement with the shroud pin 208, therefore further distal movement of the needle shroud 204 is prevented. The blocking portion 212 of the collar 202 and the shroud pin 208 together act as a latch for holding the needle shroud 204 in its retracted position during medicament delivery.

Where the device comprises a control spring (e.g., control spring 120) that exerts a spring biasing force on the needle shroud 204 to bias the needle shroud 204 distally, the biasing force will now be exerted by the needle shroud 204 on the blocking portion 212 of the collar 202 (via the shroud pin 208) rather than being exerted against the injection site against which the needle shroud 204 may be held in its retracted state by a user. As such, the user may no longer need to overcome the biasing force of the control spring to hold the device in place during medicament delivery, while the shroud pin 208 remains engaged with the blocking portion 212 and the collar 202 is prevented from rotating. This may make the device easier to handle by a user, e.g., a user with impaired dexterity who may otherwise have found the spring biasing force difficult to overcome, e.g., when holding the needle shroud 204 in a retracted position for a long period of time.

The blocking portion 212 may comprise a proximally-facing surface, such as a second cam track edge which is proximally-facing. The second cam track edge may be angled with respect to the longitudinal axis of the injection device such that the shroud pin 208 applies a force to the collar 202 during at least a portion of the extension of the needle shroud 204 out of the casing after it has been retracted, causing the collar 202 to rotate (once the collar 202 is no longer held by the plunger release mechanism) from its second position to a third (rotational) position (with respect to the needle shroud 204 and injection device body).

The end of the first angled cam track edge and the start of the second cam track edge may partially overlap in the azimuthal direction of the collar (i.e., in the circumferential direction). This prevents the shroud pin 208 being guided back along the first angled portion during extension of the needle shroud 204 after the injection has occurred.

The second portion 206B may comprise a final cam track portion 214 that is aligned with the longitudinal axis of the injection device, i.e., parallel with longitudinal axis of the injection device. Once the collar 202 has been rotated to its third position, the final cam track portion 214 guides the shroud pin 208 and needle shroud 204 in a distal axial direction such that the shroud pin 208 does not cause the collar 202 to (substantially) rotate further.

The final cam track portion 214 may contain a non-return element 216. The non-return element 216 is configured to prevent proximal retraction of the needle shroud 204 beyond the needle after the needle shroud 204 has extended from a hold position, i.e., after an injection has occurred and the device has been removed from an injection site.

In the example shown, the non-return element 216 comprises a catch. The catch comprises a resilient arm 226 extending axially (i.e., longitudinally), substantially parallel with respect to the longitudinal axis of the injection device (for example, within an aperture of the collar 202). The resilient arm 226 has a protrusion 224 at a free end that extends radially outwards. The protrusion 224 has a ramped surface 232 that is proximally-facing and a stopping surface 234 that is distally-facing with respect to the longitudinal axis of the injection device. The ramped surface 232 and stopping surface 234 are arranged such that, as the needle shroud 204 extends from its hold position to its final position, the shroud pin 208 engages and moves across the ramped surface 232 in a distal direction. A reaction force between the shroud pin 208 and the ramped surface 232 as the shroud pin 308 moves across the ramped surface 232 causes the shroud pin 208 to be deflected radially outwards and/or the non-return element 216 (e.g., the protrusion 224 and resilient arm 226) to be deflected radially inwards. After the shroud pin 208 has reached a distal edge of the ramped surface 232 and has passed the stopping surface 234, the shroud pin 208 is no longer engaged with the non-return element 216. As such, the resiliency of the needle shroud 204 and/or non-return element 216 causes the shroud pin 308 and/or non-return element 216 to be deflected back in the opposite radial direction to before, such that the shroud pin 208 at least partially overlaps the stopping surface 234 along a radius of the device. If the needle shroud 204 is now moved proximally, back into the injection device body, the shroud pin 208 is brought into abutment with the stopping surface 234 due to the overlap between the shroud pin 208 and stopping surface 234, with engagement between the stopping surface 234 and the shroud pin 208 preventing further proximal movement of the needle shroud 204 into the injection device body. As such, the needle shroud 204 is locked by the non-return element 216.

While the non-return element 216 is generally described herein as comprising a catch, it should be understood that other forms of non-return element 216 may be used instead. As an example, in some examples the non-return element 216 may comprise a protrusion 224 having a ramped surface 232 a stopping surface 234 similar to those described previously, however the protrusion 224 may be arranged to extend from an outer surface of the collar 202 that does not comprise a resilient arm 226. In other examples, a non-return element 216 may not be present (i.e., the needle shroud 204 may be permitted to retract to expose the needle, after extension of the needle shroud 204).

FIGS. 3A-E show an example of the operation of a collar 302 and needle shroud 304 of an injection device, such as the injection device 100 of FIG. 1. The collar 302 and needle shroud 304 correspond to the collar 202 and needle shroud 204 of FIG. 2.

Figure 3B:
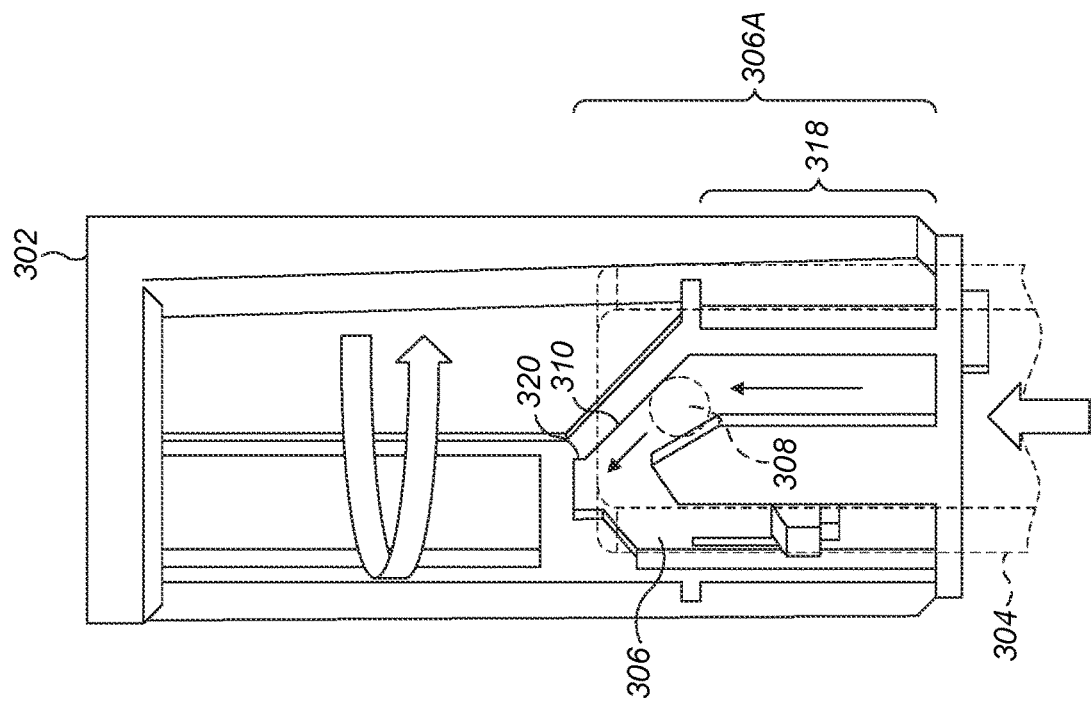
FIG. 3B shows an example of the needle shroud retracting into the injection device body.
Figure 3A:
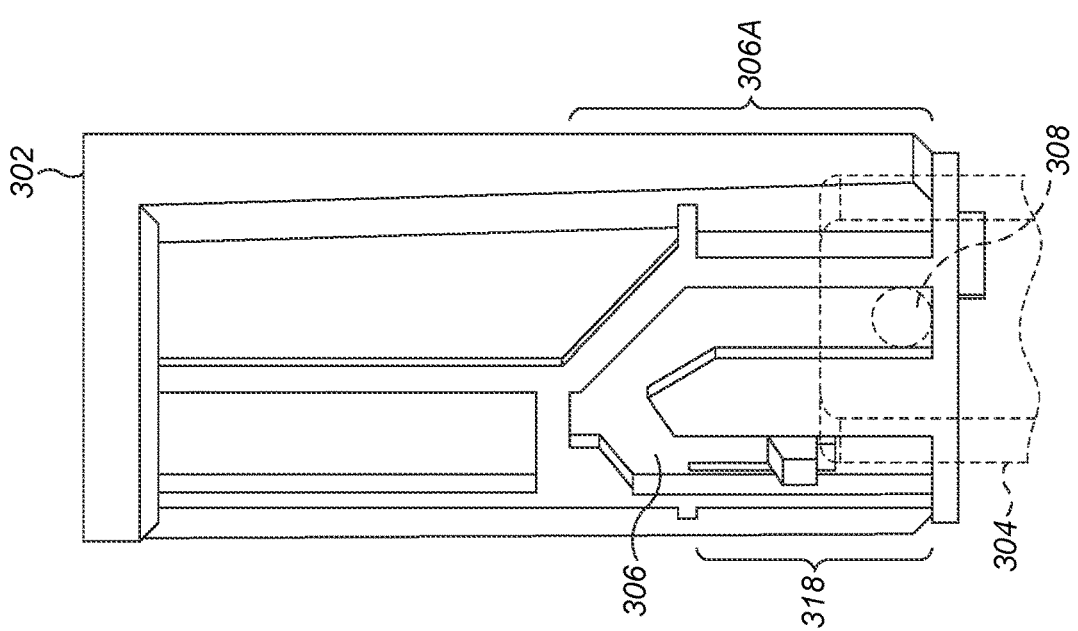
FIG. 3A shows an example of an initial configuration of the collar and needle shroud prior to retraction of the needle shroud into the injection device body.

FIG. 3A shows an example of an initial configuration of the collar 302 and needle shroud 304 prior to retraction of the needle shroud 304 into the injection device body, e.g., a pre-use position. The needle shroud 304 is in an extended position and covers a needle (not shown) of the injection device. The shroud pin 308 of the needle shroud 304 is in an initial position in the cam track 306 of the collar 302, within the initial portion 318 of the first portion 306A of the cam track 306. The shroud pin 308 is held in the initial position under a retaining force from the control spring (not shown), which biases the needle shroud 304 distally from the collar 302. The collar 302 is shown in its first (rotational) position with respect to the needle shroud 304 and injection device body and is free to rotate. In this configuration, the collar 302 may cause the plunger of the device (not shown) to be retained in an initial position, as described later in relation to FIGS. 4A and 4B. The shroud pin 308, first portion 306A and cam track 306 correspond to the shroud pin 208, first portion 206A and cam track 206 of FIG. 2.

FIG. 3B shows an example of the needle shroud 304 retracting into the injection device body, e.g., during activation of the injection device when a user is pressing the needle shroud 304 against an injection site of a subject (which may or may not be the user). As the needle shroud 304 is retracted proximally into the injection device body, the shroud pin 308 moves along the initial part 318 (corresponding to the initial portion 218) of the first portion 306A of the cam track 306 in a proximal axial direction until it reaches the first angled portion 310 (corresponding to the first angled portion 210) of the cam track 306. Further retraction of the needle shroud 304 causes the shroud pin 308 to apply a force to the first angled portion 310 of the cam track 306, which in turn causes the collar 302 to rotate from its first position to its second position. The shroud pin 308 causes the collar 302 to rotate until the shroud pin reaches an upper end of the angled portion 310, after which further retraction of the shroud 304 causes the shroud pin 308 to move into the final portion 320 of the first portion 306A of the cam track 306 and reach a hold position.

Figure 3D:
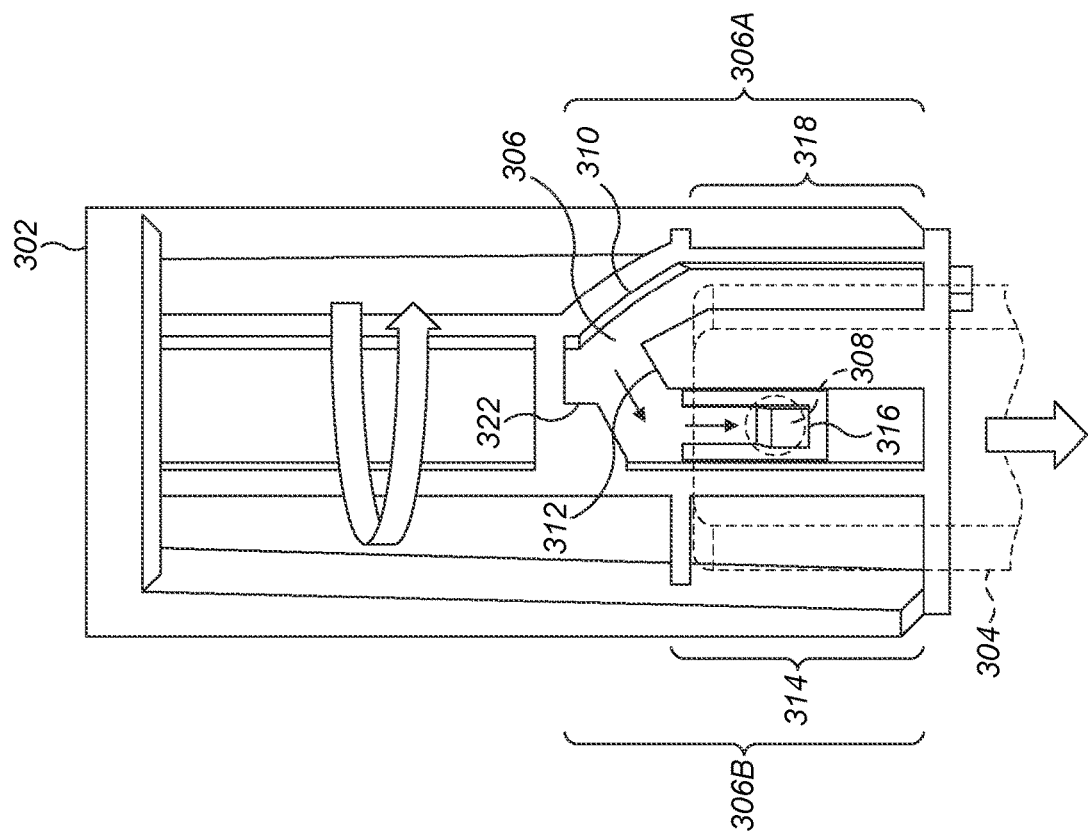
FIG. 3D shows an example of the collar moving as the needle shroud extends out of the injection device body.
Figure 3C:
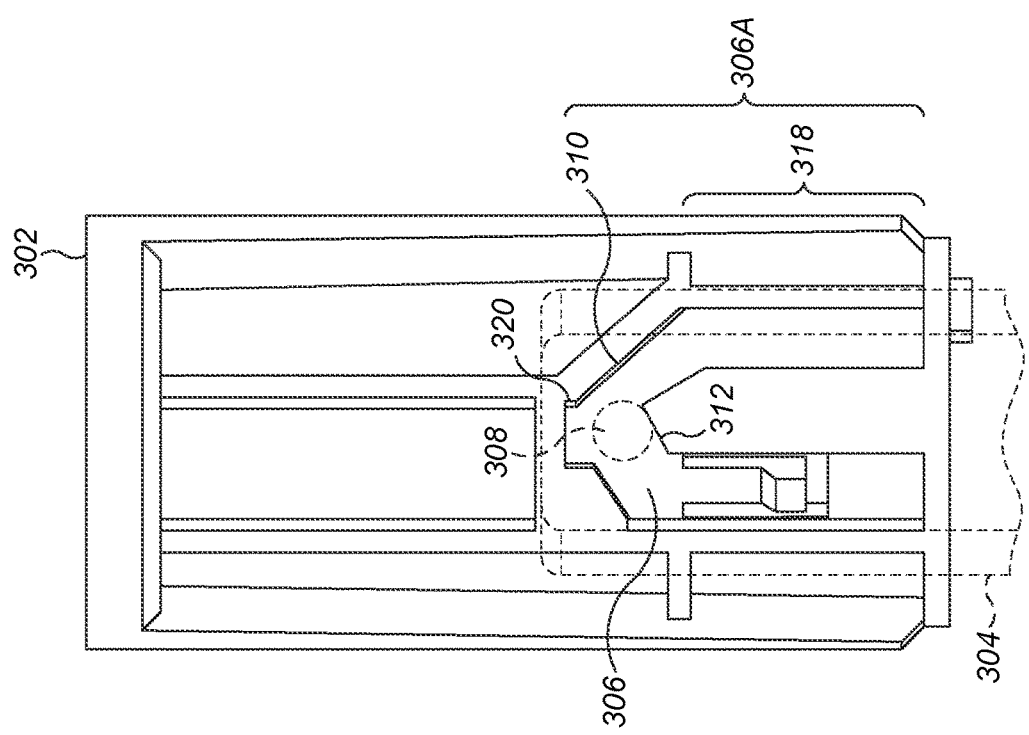
FIG. 3C shows an example of a hold configuration of the collar and needle shroud.

FIG. 3C shows an example of a hold configuration of the collar 302 and needle shroud 304, e.g., the configuration where medicament is being expelled from the injection device via a needle. The collar 302 is in its second position. In response to the collar 302 having been rotated to reach its second position, the plunger release mechanism releases the plunger to initiate medicament delivery, as described later in relation to FIGS. 4C and 4D. In response to the collar 302 reaching its second position, the plunger release mechanism also engages with the collar 302 to hold the collar 302 in its second position and prevent rotation of the collar 302, again as described later in relation to FIGS. 4C and 4D. While the collar 302 is held from rotation by the plunger release mechanism, an abutment between the shroud pin 308 and the blocking element 312 prevents extension of the needle shroud from the injection device body in a distal direction. In other words, while the collar 302 is prevented from being rotated, the blocking portion 312 prevents (via engagement with the shroud pin 308) distal axial movement of the needle shroud 304 relative to the collar 302 and the injection device body.

Where the device comprises a control spring (e.g., control spring 120) that exerts a spring biasing force on the needle shroud 304 to bias the needle shroud 304 distally, the biasing force will now be exerted by the needle shroud 304 on the blocking portion 312 of the collar 302 (via the shroud pin 308) rather than being exerted against the injection site against which the needle shroud 304 may be held in its retracted state. As such, a user may no longer need to counteract the biasing force of the control spring to hold the device in place during medicament delivery, while the shroud pin 308 remains engaged with the blocking portion 312 and the collar 302 is prevented from rotating from its second position. This may make the device easier to handle by a user, e.g., a user with impaired dexterity who may otherwise have found the spring biasing force difficult to overcome, e.g., when holding the needle shroud 304 in a retracted position for a long period of time.

FIG. 3D shows an example of the collar 302 moving as the needle shroud 304 extends out of the injection device body, e.g., during removal of the needle from the injection site after an injection has occurred. The plunger release mechanism has released the collar 302 (e.g., in response to the completion of medicament delivery) such that it is once again free to rotate from its second position, for example as described later in relation to FIGS. 4E and 4F. As the needle shroud 304 moves to extend further out of the injection device, for example under the force of the control spring, the shroud pin 308 comes into contact with the angled edge of the blocking portion 312 (if they are not already abutting). The overlap of the top of the blocking portion 312 and the top of the first angled portion 310 in the azimuthal direction prevents the shroud pin 308 from returning along the first portion 306A of the cam track 306 after the needle shroud 304 has been fully retracted. Further extension of the needle shroud 304 as it moves distally causes the shroud pin 308 to apply a force to the angled edge of the blocking portion 312, causing the collar 302 to rotate from its second position (shown in FIG. 3C) to its third position (shown in FIG. 3D), with the shroud pin 308 moving across the angled edge of the blocking portion 312 in the process.

The shroud pin 308 moves along the angled edge of the blocking portion 312 until it reaches an edge of the blocking portion 312, after which it enters a final cam track portion 314 of a second portion 306B of the cam track 306 (corresponding to the final cam track portion 214 of the second portion 206B of the cam track 206). The needle shroud 304 continues to move distally out of the injection device body, with the shroud pin 308 also moving distally through the final cam track portion 314. The shroud pin 308 engages and passes over a non-return element 316 as the needle shroud 304 continues to extend out of injection device body and the shroud pin 308 moves axially, guided by the final cam track portion 314. The non-return element 316 may be any non-return element 316 suitable for preventing distal retraction of the needle shroud 304, for example the non-return element 316 may correspond to any non-return element 216 described in relation to FIG. 2, for example having a ramped surface 232 and a stopping surface 234.

In some examples, the injection device may comprise a damper (not shown) arranged to dampen (e.g., slow) the rotation of the collar 302 from its second position (shown in FIG. 3C) to its third position (shown in FIG. 3D). The damper may be coupled to, or otherwise arranged between, the collar 302 and another portion of the device such as a rear casing (e.g., rear casing 114) or housing (e.g., outer casing 102). As an example, the damper may be a viscous damper, for example comprising a viscous fluid between the collar 302 and a rotationally fixed part of the injection device. The damper may provide a speed dependent torque that partially counteracts rotation of the collar 302 from its second position to its third position. By slowing the rotation of the collar 302, the time it takes for the shroud pin 308 to move along the angled edge of the blocking portion 312 until it enters the final cam track portion 314 can be increased, which may delay the sudden increase in biasing force transferred to the injection site by the control spring (via the needle shroud 304) once the collar 302 has been released for rotation by the plunger release mechanism. It may be desirable that the damper does not dampen rotation of the collar 302 from its first position to its second position, so that it does not add to the activation force required to initiate medicament delivery.

Figure 3E:
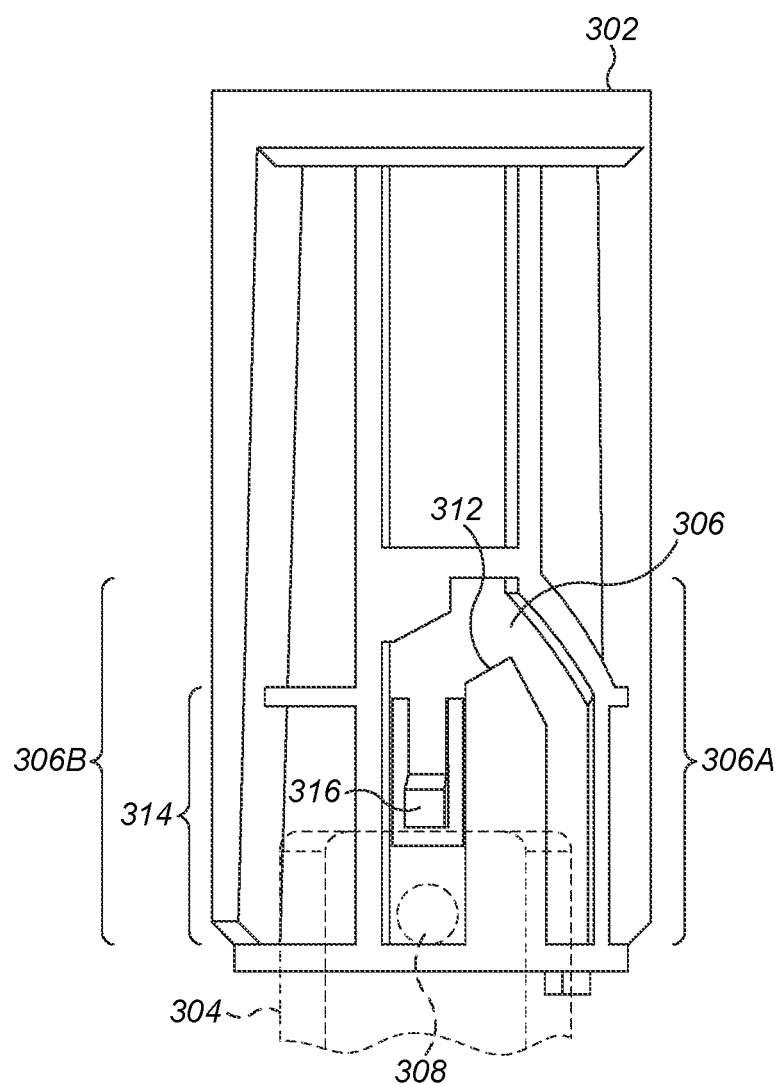
FIG. 3E shows an example of a locked configuration of the collar and needle shroud.

FIG. 3E shows an example of a locked configuration of the collar 302 and needle shroud 304, e.g., the configuration after the needle shroud 304 has extended from the device body after retraction. In this configuration, the shroud pin 308 is locked in a final portion of the cam tack 306 by the non-return element 316, which in this example comprises a catch (e.g., as described in relation to FIG. 2). The non-return element 316 prevents further retraction of the needle shroud 304 into the injection device body (and thus exposure of the needle) by engaging with the shroud pin 308 when the needle shroud 304 is moved in the proximal axial direction.

FIGS. 4A-F show examples of a plunger release mechanism cooperating with a collar of an injection device, such as the collar 302.

Figure 4B:
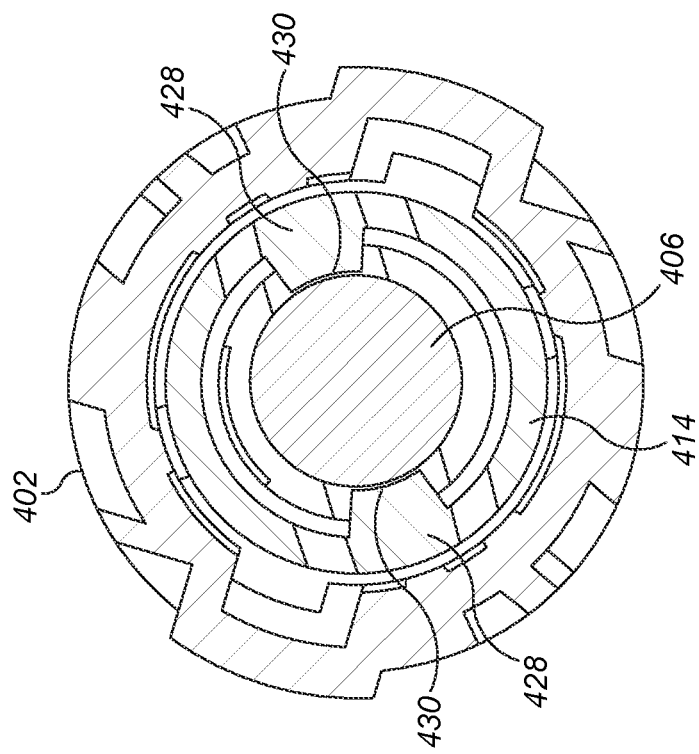
FIG. 4B shows an example of a cross section of an injection device in a plane through the teeth of the toothed beams prior to release of the plunger.
Figure 4A:
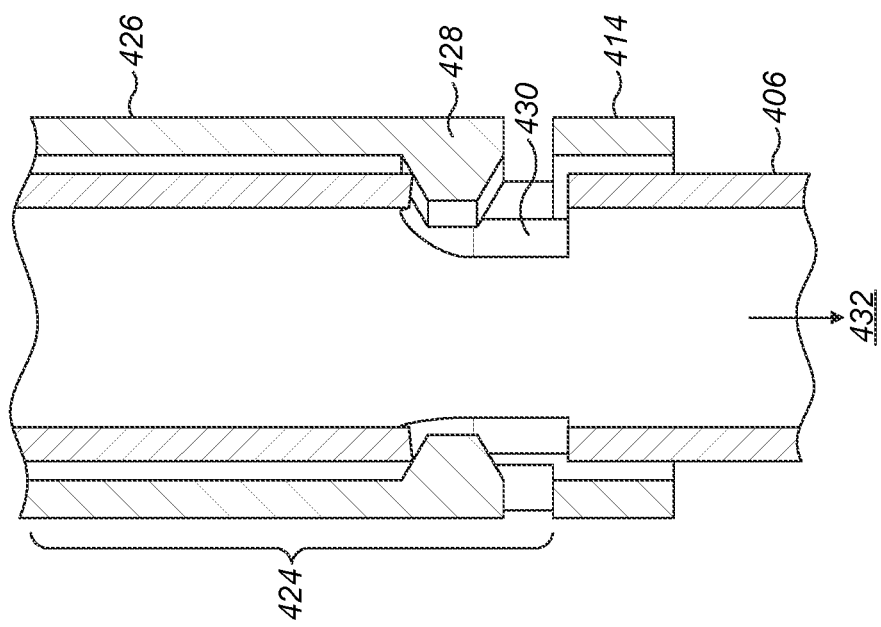
FIG. 4A shows a cut-away view of an example of a plunger and a rear casing prior to release of the plunger.

FIG. 4A shows a cut-away view of an example of a plunger 406 and a rear casing 414, which may correspond to the plunger 106 and rear casing 114 of FIG. 1, prior to release of the plunger 406. The rear casing 414 comprises one or more (e.g., two or three) toothed beams 424, which may form part of the plunger release mechanism. Each toothed beam 424 comprises a flexible arm 426 and a tooth 428, wherein the flexible arm(s) 426 may extend substantially parallel to the longitudinal axis of the injection device. The plunger 406 comprises one or more recesses 430 corresponding to the one or more toothed beams 424, which can each engage with a tooth 428 of a respective toothed beam 424. In some examples, the recesses 430 and toothed beams 424 are evenly spaced around the plunger 406 and rear casing 414 respectively, e.g., spaced at 180 degrees around the plunger 406 and rear casing 414 for two recesses 430 and teeth 428, spaced at 120 degrees around the plunger 406 and rear casing 414 for three recesses 430 and teeth 428, etc. While held in the recesses 430 (e.g., by the collar 402, as described in relation to FIG. 4B), the teeth 428 of the toothed beams 424 hold the plunger 406 to prevent the plunger 406 from moving in the distal direction 432 to dispense medicament.

The one or more recesses 430 and/or corresponding teeth 428 are shaped to urge the toothed beams 424 outwards (as shown in FIG. 4C) when a force is applied to the plunger 406 in the distal direction 432. For example, each tooth 428 may comprise a bevel (e.g., be chamfered) at its proximal end (and may, in some examples also be bevelled at its distal end). When the plunger 406 moves/is urged in the distal direction 432 (e.g., under the force of a drive spring 122), an upper (i.e., proximal) portion of each recess 430 contacts the bevel of its respective tooth 428 and applies an outward force to the respective toothed beam 424. In the absence of retention, e.g., by a collar 402, this causes the toothed beams 424 to flex outwards, releasing the plunger 406 and allowing an injection to proceed.

FIG. 4B shows an example of a cross section of an injection device in a plane through the teeth 428 of the toothed beams 424 prior to release of the plunger 406. The portion of the rear casing 414 comprising the toothed beams is surrounded by the collar 402 of the injection device, which prevents the teeth 428 of the toothed beams from flexing outwards due to the force applied on them by the recess 430 of the plunger 406. Since the toothed beams are prevented from flexing outwards, they do not prevent the collar 302 from being rotated. As such, the collar 402 is free to rotate from its first (rotational) position shown in FIG. 4B to its second (rotational) position shown in FIG. 4D in response to retraction of a needle shroud into the injection device body (e.g., as described in relation to FIGS. 2 and 3B).

FIG. 4C shows a cut-away view of the plunger 406 and rear casing 414 of FIG. 4A during medicament delivery. As the collar 402 rotates during retraction of the needle shroud into the injection device, one or more recesses 434 (as shown in FIG. 4D) in the inner surface of the collar 402 rotate over the teeth 428 of the toothed beams 424 until they are each in radial alignment with a respective tooth 428. This provides space for the toothed beams 424 to be forced outwards in a radial direction by their respective plunger recesses 430, thereby releasing the plunger 406. The one or more recesses 434 may be arranged to allow release of the plunger 406 when the collar 402 is in its second position and the shroud pin (e.g., shroud pin 308) of the needle shroud enters the final part of the first portion of the cam track (e.g. cam track 306). FIG. 4C shows the plunger 406 having moved in the distal direction 432 with respect to the rear casing 414 under the force of a drive spring, with the toothed beams 424 held in their radially deflected positions by contact between the teeth 428 and the outer surface of the plunger 406.

FIG. 4D shows an example of a cross section of an injection device in a plane through the teeth 428 of the toothed beams during release of the plunger 406 and medicament delivery, as previously described in relation to FIG. 4C. FIG. 4D shows the collar 402 in its second position, having rotated during retraction of the needle shroud into the injection device to bring the one or more recesses 434 in the inner surface of the collar 402 into alignment with the teeth 428 of the toothed beams 424. The toothed beams 424 have been forced outwards in a radial direction by their respective plunger recesses 430, thereby releasing the plunger 406. As the toothed beams 424 are deflected radially, the distal end of each toothed beam 424 engages a respective recess 434 in the inner surface of the collar 402 to hold the collar 402 in its second position and prevent rotation of the collar 402. While the collar 402 is held in its second position by the toothed beams 242, a blocking portion (i.e., blocking portion 312) of the collar 402 prevents extension of the needle shroud from the injection device body as previously described in relation to FIG. 3C.

During medicament delivery, the plunger 406 continues to move axially in the distal direction 432 under the bias of the drive spring, with the toothed beams 424 being prevented from disengaging from the recesses 434 (and therefore prevented from releasing the collar 402 to rotate) due to contact between the toothed beams 424 and the outside surface of the plunger 406. During this period, rotation of the collar 402 is prevented and therefore distal movement of the needle shroud 404 is prevented by the blocking element of the collar 402.

Figure 4F:
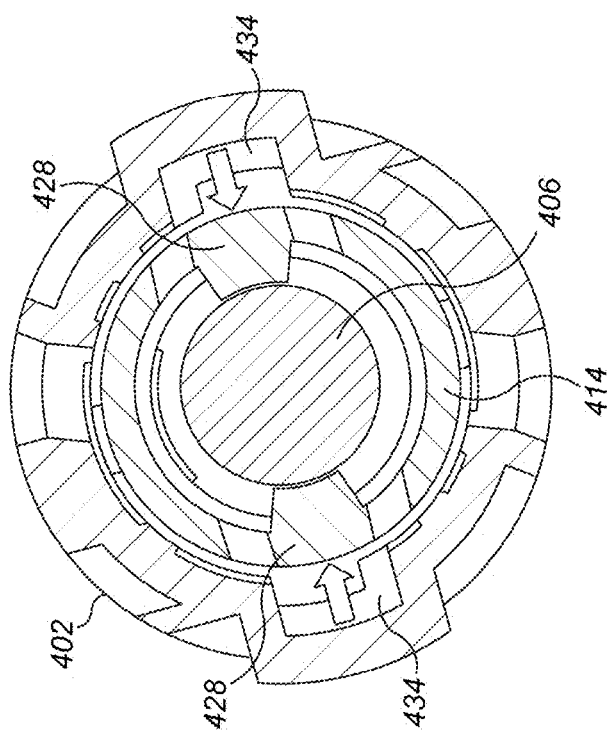
FIG. 4F shows an example of a cross section of the injection device of FIG. 4D in a plane through the teeth of the toothed beams after an injection is completed.
Figure 4E:
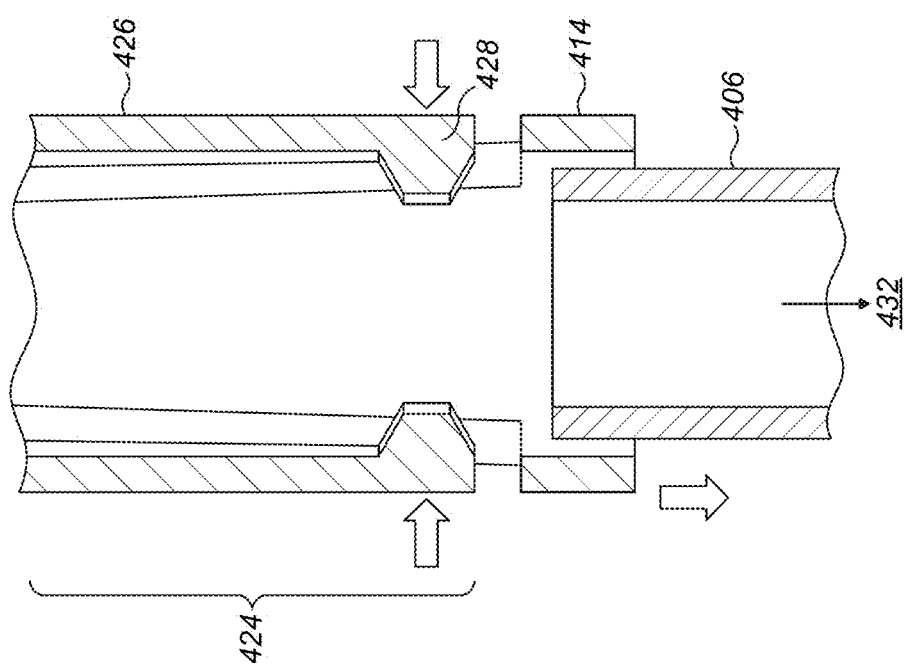
FIG. 4E shows a cut-away view of an example of the plunger and rear casing after an injection is completed.

FIG. 4E shows a cut-away view of the plunger 406 and rear casing 414 of FIGS. 4A and 4C after medicament delivery is complete. The plunger 406 has continued moving in the distal direction 432 until the toothed beams 424 are no longer held in their deflected state by the plunger 406. FIG. 4E shows a proximal end of the plunger 406 having moved distally past the toothed beams 424 such that the toothed beams 424 are no longer in contact with (and deflected by) the outside surface of the plunger 406, and therefore the toothed beams 424 move inwards in a radial direction (e.g. due to resiliency of the toothed beams 424). However, in other examples the toothed beams 424 may move inwards in a radial direction in response to the teeth 428 being brought into alignment with respective recesses (not shown) in the plunger 406, rather than reaching a proximal end of the plunger 406.

The toothed beams 424 and the plunger 406 may be configured such that the toothed beams 424 are allowed to move radially inwards and therefore disengage their respective recesses 434 in response to medicament delivery being completed (i.e., when the plunger 406 has distally moved a predetermined distance to dispense a predetermined volume of medicament).

FIG. 4F shows an example of a cross section of an injection device in a plane through the teeth 428 of the toothed beams after medicament delivery is complete, as previously described in relation to FIG. 4E. The one or more toothed beams 424 have moved radially inwards, disengaging from their respective one or more recesses 434 and thereby once again allowing rotation of the collar 402 with respect to the plunger 406 and rear casing 414. As such, the collar 402 is now free to rotate from its second position to its third position, allowing the needle shroud to extend from the injection device body, for example as previously described with respect to FIGS. 2 and 3D.

Figure 5:
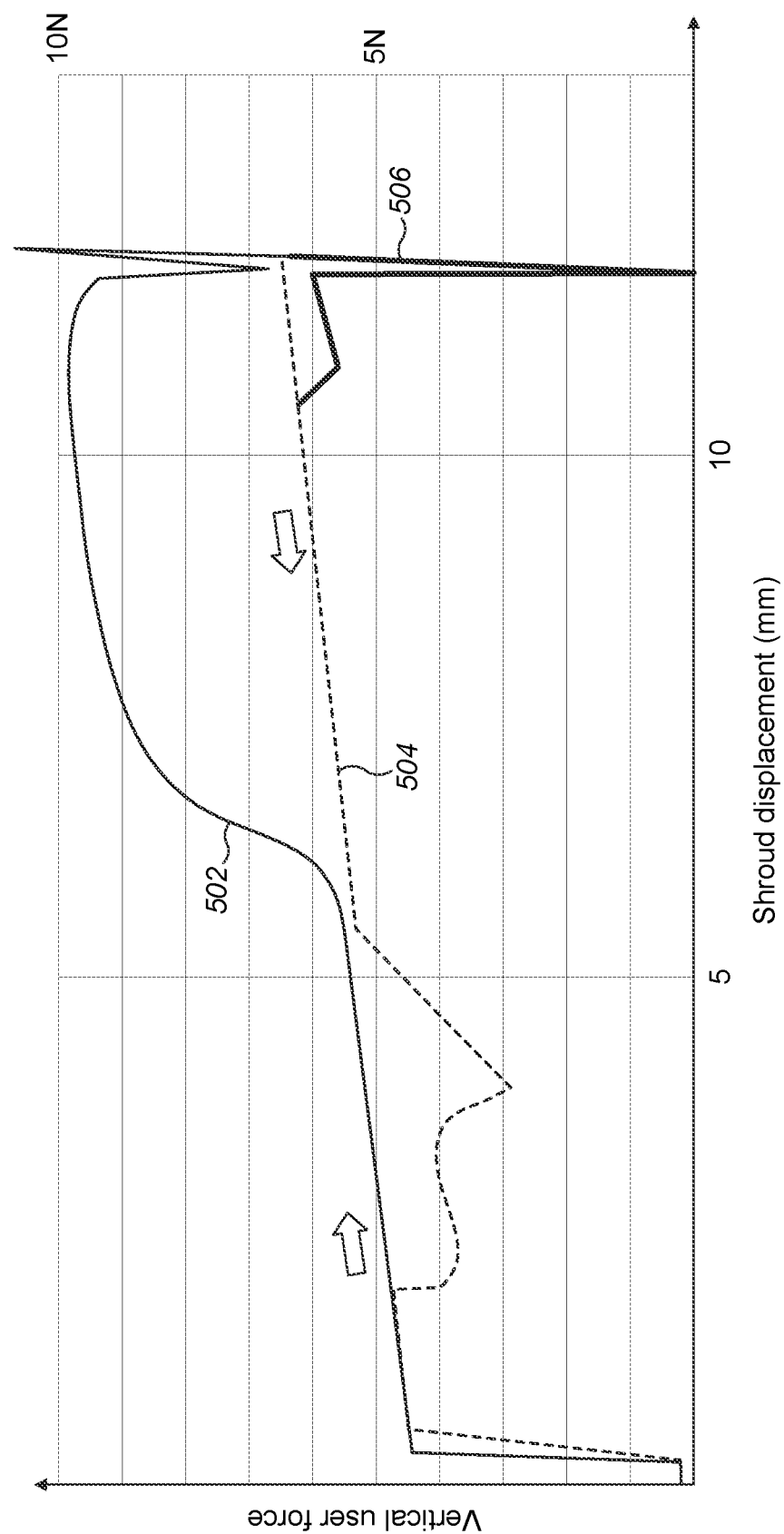
FIG. 5 shows an example comparison of force profiles of an injection device during use.

FIG. 5 shows an example comparison of force profiles of a prior art injection device and an injection device according to one or more embodiments of the present disclosure (e.g. as described in relation to FIGS. 1, 2, 3A-E, 4A-F and/or 6) during use. The graph shows a magnitude of a vertical force applied (in Newtons, N) by a user as a function of needle shroud displacement (in mm) during insertion and removal of a device from a subject's body for both a prior art injection device (e.g., without having a blocking element) and a device using a collar having a blocking element as described herein.

The first trace 502 shows the force profile of the activation force of both a prior art device and an injection device according to one or more embodiments of the present disclosure, when a user is pushing the device onto a subject's body. The second trace 504 shows the force profile of a prior art device when a user is removing the device from a subject's body. The force profile of an injection device according to embodiments of the present disclosure, when the user is removing the device from a subject's body, is similar to the second trace 504, except for the deviation near maximal displacement of the shroud as indicated by the third trace 506.

The third trace 506 shows that the user force required by a user to overcome the force applied to the needle shroud by the control spring can be reduced to zero when using embodiments of the present disclosure. Since a blocking element of the collar prevents movement of the needle shroud out of the injection device body while the collar is held in its second position, the biasing force provided by the control spring to the needle shroud is exerted on the collar rather than the subject. The subject therefore does not need to overcome the biasing force applied by the control spring to the needle shroud while the collar is held in its second position (e.g. during plunger movement). This can make it easier for a user to hold the device steady against the injection site while medicament is being delivered, which may be e.g., beneficial for users with impaired dexterity.

Once medicament delivery is complete and the collar has been released by the plunger release mechanism for rotation, the user may remove the device from the injection site. Once the shroud pin is brought out of engagement with the blocking element during extension of the needle shroud, at least a portion of the biasing force provided by the control spring to the needle shroud may once again be transferred to the injection site. The force profile may therefore leave the third trace and follow the reminder of the second trace until the device is fully removed from the injection site.

Figure 6:
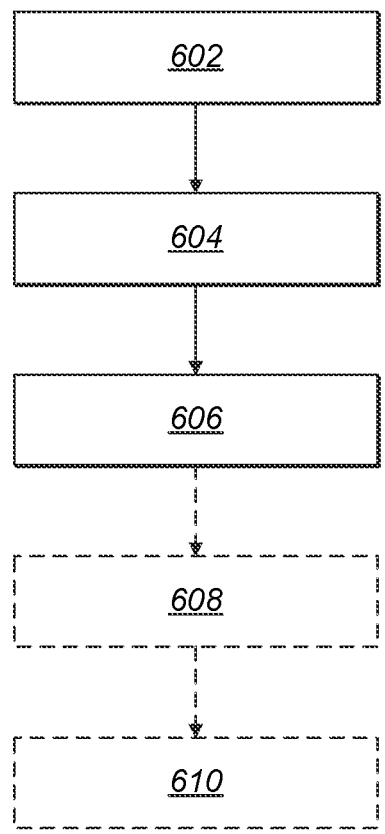
FIG. 6 shows a flow diagram of an example method of holding a needle shroud of an injection device during medicament delivery.

FIG. 6 shows a flow diagram of an example method for holding the needle shroud of an injection device during medicament delivery. The method corresponds to the operations described in relation to FIGS. 3A-E and FIGS. 4A-F.

At operation 602, during retraction of a needle shroud into an injection device body, a shroud pin of the needle shroud is guided from an initial position to a hold position using a first portion of a cam track of an injection device collar, the guiding causing the injection device collar to rotate relative to the injection device body from a first position to a second position.

The first portion of the cam track comprises a first angled portion between the initial position and the hold position that is angled to cause rotation of the collar from the first position to the second position when the shroud pin is urged against it. The first portion of the cam track may further comprise an initial portion that is parallel to a longitudinal axis of the injection device, and that extends from the initial position to a start of the first angled portion. The first portion of the cam track may further comprise a final part that is parallel to a longitudinal axis of the injection device, and that extends from the end of the first angled portion. The hold position may lie in the final part of the first portion of the cam track.

At operation 604, the collar is held in the second position. The collar may be held in the second position by a plunger release mechanism of the injection device. In some examples, the method comprises causing release of a plunger of the injection device when the shroud pin reaches the final part of the first portion of the cam track and the collar is in the second position. For example, when the collar rotation is such that the shroud pin enters the final part of the first portion of the cam track and the collar is in its second position, one or more recesses in an inner surface of the collar may align with respective teeth on one or more toothed beams of a rear casing of the injection device, allowing toothed beams and respective teeth to be urged radially outwards by respective recesses on the plunger such that the teeth engage corresponding recesses in an inner surface of the collar. The engagement between the one or more teeth and the collar prevents rotation of the collar, thereby holding the collar in its second position. The holding of the collar may be only temporary, for example during a movement of the plunger to dispense the medicament.

At operation 606, while the collar is held in the second position, extension of the needle shroud from the injection device body is prevented using a blocking portion of the cam track, for example as previously described in relation to FIGS. 2 and 3C. Prevention of the needle shroud moving distally (i.e. extending from the injection device body) may be brought about by an abutment between the shroud pin and the blocking portion.

At optional operation 608, the collar is released such that it is free to rotate from its second position. The collar may be released to rotate by the plunger release mechanism, for example as previously described in relation to FIGS. 2, 3D, 4E and 4F. The collar may be released to rotate by the plunger release mechanism responsive to completion of a movement of the plunger to dispense the medicament.

At optional operation 610, after the collar is released such that it is free to rotate, and during extension of the needle shroud from the injection device body subsequent to the retraction, the shroud pin is guided from the hold position to a final position using a second portion of the cam track of the injection device collar, the guiding causing the injection device collar to rotate relative to the injection device body from its second position to a third position. The rotation is in the same direction (e.g., clockwise or anticlockwise) as the rotation caused by the first portion of a cam track during retraction of the needle shroud.

The second portion of the cam track comprises the blocking portion, which may be angled to cause rotation of the collar from the second position to the third position when the shroud pin is urged against it. The second portion of the cam track may further comprise an initial portion that is parallel to a longitudinal axis of the injection device, and that includes the hold position and extends to a start of the second angled portion. The initial portion of the second portion of the cam track at least partially overlaps with the final part of the first portion of the cam track.

Subsequent to the extension of the needle shroud, further retraction of the needle shroud into the injection device body may be prevented using a non-return element, for example any non-return element 216 or 316 as described herein.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N—(ω-carboxyheptadecanoyl)-des(B30) human insulin and B29-N—(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom. Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

Those of skill in the art will understand that modifications (additions and/or removals) of various components of the embodiments described herein may be made without departing from the full scope and spirit of the present invention, which encompass such modifications and any and all equivalents thereof.

LIST OF REFERENCE NUMBERS

100—injection device
102—outer casing/housing
104—reservoir
106—plunger
108—collar
110—cap
112—longitudinal axis
114—rear casing
116—needle
118—needle shroud/sleeve/cover
120—control spring
122—drive spring
124—stopper
126—distal end
128—proximal end
202—collar
204—needle shroud/sleeve/cover
206—cam track
206A—first portion of cam track
206B—second portion of cam track
208—shroud pin
210—first angled portion
212—blocking portion
214—final portion of second portion of the cam track
216—non-return element
218—initial portion of first portion of the cam track
220—final portion of first portion of the cam track
222—initial portion of second portion of the cam track
224—protrusion
226—resilient arm
232—ramped surface
234—stopping surface
302—collar
304—needle shroud/sleeve/cover
306—cam track
306A—first portion of cam track
306B—second portion of cam track
308—shroud pin
310—first angled portion
312—blocking portion
316—non-return element
318—initial portion of first portion of the cam track
320—final part of first portion of the cam track
322—initial part of second portion of the cam track
402—collar
406—plunger
414—rear casing
424—toothed arm
426—flexible arm
428—tooth
430—recess in plunger
434—recess in collar
502—first trace
504—second trace
502—third trace
602—(first) operation of method
604—(second) operation of method
606—(third) operation of method
608—(fourth) operation of method
610—(fifth) operation of method

The invention claimed is:

1. An injection device comprising:
    an injection device body;
    a plunger comprising one or more recesses;
    a plunger release mechanism comprising one or more toothed beams, wherein each of the one or more toothed beams comprise a tooth engageable with a respective recess of the one or more recesses of the plunger;
    a biasing means for biasing the plunger in a distal direction of the injection device, wherein the one or more recesses and/or the one or more teeth are shaped to urge the one or more toothed beams out of the one or more recesses when the plunger is moved in the distal direction of the injection device;
    a needle shroud retractable into the injection device body comprising a shroud pin; and
    a collar rotatable with respect to the injection device body and comprising a cam track engageable with the shroud pin,
    wherein the cam track comprises:
        a first portion configured to, during retraction of the needle shroud into the injection device body, guide the shroud pin from an initial position to a hold position and cause the collar to rotate relative to the injection device body from a first position to a second position; and
        a second portion configured to, during extension of the needle shroud from the injection device body subsequent to the retraction, guide the shroud pin from the hold position to a final position and cause the collar to further rotate relative to the injection device body from the second position to a third position, and
    wherein the second portion comprises a blocking portion configured to prevent extension of the needle shroud from the injection device body when the collar is held in the second position, wherein an internal surface of the collar comprises one or more recesses arranged to allow the one or more toothed beams to flex outwardly when the collar is rotated to the second position to release the plunger, and wherein the one or more toothed beams are configured to engage the one or more recesses in the internal surface of the collar when the collar is in the second position, to hold the collar in the second position and prevent rotation of the collar.

2. The injection device of claim 1, wherein the first portion of the cam track comprises a first angled cam track edge arranged to convert at least a portion of proximal axial motion of the needle shroud into rotational motion of the collar.

3. The injection device of claim 1, wherein the blocking portion comprises a second angled cam track edge arranged to convert at least a portion of distal axial motion of the needle shroud into rotational motion of the collar.

4. The injection device of claim 1, wherein the collar surrounds the one or more toothed beams to prevent the toothed beams from flexing outwardly when the collar is in the first position, thereby holding the plunger.

5. The injection device of claim 1, wherein the one or more toothed beams are configured to be held in engagement with the one or more recesses in the internal surface of the collar by an outer surface of the plunger during distal movement of the plunger.

6. The injection device of claim 1, wherein the injection device further comprises a control spring to bias the needle shroud towards an extended position.

7. The injection device of claim 1, wherein the shroud pin extends inwardly from the needle shroud in a radial direction.

8. The injection device of claim 1, wherein the injection device further comprises a needle, and wherein the needle shroud is arranged to shroud the needle when in an extended position.

9. The injection device of claim 1, wherein the injection device further comprises a syringe containing a medicament.

10. A collar for an injection device comprising a cam track engageable with a shroud pin of a needle shroud, wherein the cam track comprises:
    a first portion configured to, during retraction of the needle shroud into an injection device body of the injection device, guide the shroud pin from an initial position to a hold position and cause the collar to rotate relative to the injection device body from a first position to a second position; and
    a second portion configured to, during extension of the needle shroud from the injection device body subsequent to the retraction, guide the shroud pin from the hold position to a final position and cause the collar to further rotate relative to the injection device body from the second position to a third position, wherein an internal surface of the collar comprises one or more recesses arranged to allow one or more toothed beams of a plunger release mechanism to flex outwardly when the collar is rotated to the second position to release a plunger, and
    wherein the second portion comprises a blocking portion configured to prevent extension of the needle shroud from the injection device body when the collar is held in the second position, wherein the blocking portion comprises a second angled cam track edge arranged to convert at least a portion of distal axial motion of the needle shroud into rotational motion of the collar, wherein the one or more recesses in the internal surface of the collar are configured to be engaged by the one or more toothed beams when the collar is in the second position, to hold the collar in the second position and prevent rotation of the collar.

11. The collar of claim 10, wherein the first portion of the cam track comprises a first angled cam track edge arranged to convert at least a portion of proximal axial motion of the needle shroud into rotational motion of the collar.

12. The collar of claim 10, wherein the collar is arranged to surround one or more toothed beams of the plunger release mechanism to prevent the toothed beams from flexing outwardly when the collar is in the first position, thereby holding the plunger.

13. The collar of claim 10, wherein the shroud pin extends inwardly from the needle shroud in a radial direction.

14. A method for holding a needle shroud of an injection device during medicament delivery, the method comprising:
    during retraction of the needle shroud into an injection device body of the injection device, guiding a shroud pin of the needle shroud from an initial position to a hold position using a first portion of a cam track of an injection device collar, the guiding causing the injection device collar to rotate relative to the injection device body from a first position to a second position, wherein an internal surface of the injection device collar comprises one or more recesses arranged to allow one or more toothed beams of a plunger release mechanism to flex outwardly when the injection device collar is rotated to the second position to release a plunger of the injection device, wherein the one or more toothed beams each comprise a tooth engageable with a respective recess of one or more recesses of the plunger, wherein the one or more recesses and/or the one or more teeth are shaped to urge the one or more toothed beams out of the one or more recesses when the plunger is moved in a distal direction of the injection device;

holding the injection device collar in the second position, wherein the injection device collar is held in the second position by the plunger release mechanism of the injection device; and while the injection device collar is held in the second position, preventing extension of the needle shroud from the injection device body using a blocking portion of the cam track, wherein the blocking portion comprises a second angled cam track edge arranged to convert at least a portion of distal axial motion of the needle shroud into rotational motion of the injection device collar, wherein the one or more recesses in the internal surface of the injection device collar are configured to be engaged by the one or more toothed beams when the injection device collar is in the second position, to hold the injection device collar in the second position and prevent rotation of the injection device collar.

15. The method of claim 14, further comprising releasing the injection device collar such that it is free to rotate from its second position, responsive to completion of a movement of the plunger of the injection device to dispense a medicament.

16. The method of claim 15, further comprising:
after the injection device collar is released such that it is free to rotate, and during extension of the needle shroud from the injection device body subsequent to the retraction, guiding the shroud pin from the hold position to a final position using a second portion of the cam track of the injection device collar, wherein the second portion comprises the blocking portion, the guiding causing the injection device collar to rotate relative to the injection device body from its second position to a third position.

17. The method of claim 16, wherein the rotation of the injection device collar from the first position to the second position is in the same direction as the rotation of the injection device collar from the second position to the third position.

18. The method of claim 14, wherein the first portion of the cam track comprises a first angled cam track edge arranged to convert at least a portion of proximal axial motion of the needle shroud into rotational motion of the injection device collar.

19. The method of claim 14, further comprising dispensing a medicament from a syringe of the injection device.

* * * * *